United States Patent [19]
Sakaguchi et al.

[11] Patent Number: 5,395,553
[45] Date of Patent: Mar. 7, 1995

[54] LIQUID CRYSTALLINE COMPOUNDS, LIQUID CRYSTAL COMPOSITIONS CONTAINING THE SAME AND USE THEREOF

[75] Inventors: Kazuhiko Sakaguchi, Toyonaka; Tohru Kitamura, Kyoto, both of Japan

[73] Assignee: Daiso Co., Ltd., Osaka, Japan

[21] Appl. No.: 180,380

[22] Filed: Jan. 12, 1994

Related U.S. Application Data

[62] Division of Ser. No. 557,777, Jul. 26, 1990, Pat. No. 5,338,482.

[30] Foreign Application Priority Data

Jul. 27, 1989 [JP] Japan ................... 1-195729

[51] Int. Cl.⁶ ............. C09K 19/34; C07D 239/02; C07D 307/26
[52] U.S. Cl. .............. 252/299.61; 252/299.01; 252/299.66; 544/298; 544/335; 549/323; 549/322
[58] Field of Search ............ 252/299.61, 299.66, 252/299.01; 549/322, 323; 544/298, 335

[56] References Cited

U.S. PATENT DOCUMENTS

| | | | |
|---|---|---|---|
| 4,596,667 | 6/1986 | Inukai et al. | 252/269.65 |
| 4,621,901 | 11/1986 | Petrzilka et al. | 252/299.61 |
| 4,668,425 | 5/1987 | Nogorikawa et al. | 252/299.61 |
| 4,874,542 | 10/1989 | Higuchi et al. | 252/299.61 |
| 4,906,401 | 3/1990 | Dübal et al. | 252/299.61 |
| 4,909,957 | 3/1990 | Sakaguchi et al. | 252/289.61 |
| 4,913,532 | 4/1990 | Yoshida et al. | 252/299.01 |
| 5,061,398 | 10/1991 | Takehara et al. | 252/299.61 |
| 5,151,214 | 9/1992 | Koden et al. | 252/299.61 |
| 5,215,678 | 6/1993 | Koden et al. | 252/299.61 |
| 5,256,330 | 10/1993 | Koyama et al. | 252/299.61 |
| 5,338,482 | 8/1994 | Sakaguchi et al. | 252/299.61 |

FOREIGN PATENT DOCUMENTS

| | | |
|---|---|---|
| 031932 | 7/1981 | European Pat. Off. . |
| 0306919 | 3/1989 | European Pat. Off. . |
| 2292766 | 12/1987 | Japan . |
| 3156752 | 6/1988 | Japan . |

*Primary Examiner*—Shean Wu
*Attorney, Agent, or Firm*—Foley & Lardner

[57] ABSTRACT

Liquid crystalline compounds having an optically active γ-lactone ring of the general formula (A):

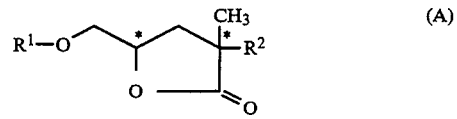

wherein $R^1$ is a group selected from the class consisting of

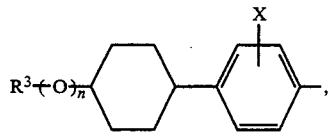

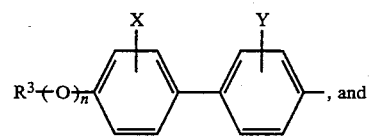

, and

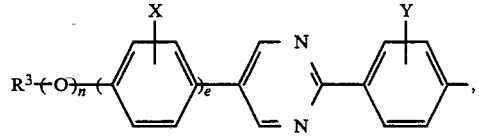

, n and e are each independently 0 or 1, $R^3$ is an alkyl group having 1 to 15 carbon atoms or an alkenyl group having 2 to 15 carbon atoms, said alkyl and alkenyl groups having each optionally one or more asymmetric carbon atoms, X and Y are each hydrogen atom, a halogen atom or a cyano group, $R^2$ is an alkyl group having 1 to 15 carbon atoms or an alkenyl group having 2 to 15 carbon atoms, said alkyl and alkenyl groups having each optionally one or more asymmetric carbon atoms, and * means an asymmetric carbon atom, a liquid crystal composition containing the same and an element for opto-electronics devices comprising the liquid crystal composition.

3 Claims, No Drawings

LIQUID CRYSTALLINE COMPOUNDS, LIQUID CRYSTAL COMPOSITIONS CONTAINING THE SAME AND USE THEREOF

This application is a divisional of Ser. No. 07/557,777 filed Jul. 26, 1990, now U.S. Pat. No. 5,338,482.

This invention relates to liquid crystalline compounds, liquid crystal compositions containing the same and use thereof as an element for display devices or an element for opto-electronics devices. The liquid crystalline compounds of this invention include not only the compounds which can exhibit the liquid crystal phase by themselves but also the compounds which do not exhibit the liquid crystal phase alone but are useful as a component of liquid crystal compositions.

PRIOR ART

Liquid crystals have widely been used as a material for display devices, where a TN (Twisted Nematic) type display system is usually employed. This TN display system has such advantages that it has less electric consumption, it gives less eye fatigue because it is a receptor type, and the like, but on the other hand, this system is disadvantageous in that the driving force is very weak because it is driven mainly on the basis of anisotropy of dielectric constant and it is slow in response speed, and hence, this system can not be applied to the devices which require high response speed.

Liquid crystal having ferroelectricity has first been found by R. B. Meyer et al. in 1975 (cf. J. Physique, 36, L-69, 1975). This liquid crystal is driven by a comparatively large force derived from spontaneous polarization and shows extremely high response speed and has also good memory. Owing to such excellent properties, the ferroelectric liquid crystal has been noticed as a new type of display element. In order to exhibit the ferroelectricity, the liquid crystalline compounds should show chiral smectic C phase (SmC* phase) and thus should contain at least one asymmetric carbon atom in the molecule. It is also necessary to have a dipole moment in the direction vertical to the long axis of the molecule.

A ferroelectric liquid crystal DOBAMBC synthesized by Meyer et al. has the following formula:

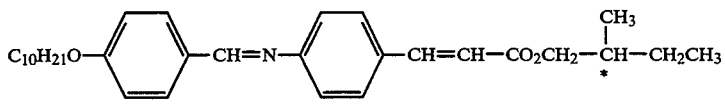

and satisfies the above conditions, but it contains a Schiff base and hence is chemically unstable and show such a low spontaneous polarization as $3 \times 10^{-9}$ C/cm². Since then, there have been synthesized many ferroelectric liquid crystalline compounds, but any practically useful compound having sufficiently high response speed has never been found.

Among the known ferroelectric liquid crystalline compounds, DOBA-1-MBC which has the asymmetric carbon atom at the position nearer to the carbonyl group than in DOBAMBC and has the following formula:

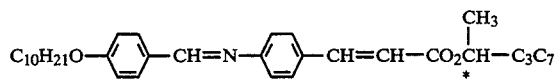

shows a spontaneous polarization of $5 \times 10^{-8}$ C/cm² which is larger than that of DOBAMBC. It is assumed that this will be caused by the following difference. That is, the asymmetric carbon atoms and the dipole which are important factors for the appearance of ferroelectricity are positioned close to each other, and thereby, the free rotation of the dipole moiety of molecule is depressed and then the orientation of the dipole is increased. Thus, it is assumed that the known ferroelectric liquid crystalline compounds can not give satisfactory spontaneous polarization and high response speed because the asymmetric carbon atom having an inhibitory action of the free rotation of the molecule is present on the linear chain in the known ferroelectric liquid crystalline compounds and hence the free rotation of the molecule can not completely be inhibited and the dipole moiety can not be fixed.

U.S. Pat. No. 4,909,957 issued on Mar. 20, 1990 (corresponding European Patent Publication No. 306919 published on Mar. 15, 1989) discloses liquid crystalline compounds having an optically active γ-lactone ring of the formula:

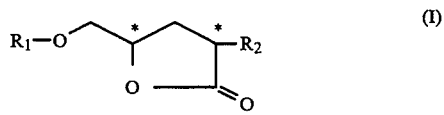

(I)

wherein $R_1$ is a group selected from the group consisting of

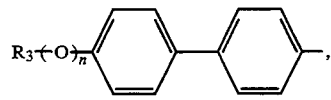

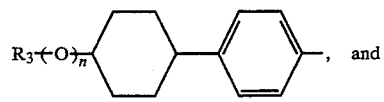
, and

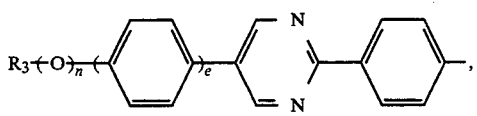
, n and e are each independently 0 or 1, $R_3$ is an alkyl group having 1 to 15 carbon atoms, $R_2$ is a group of the formula: $-(CO)_m-R_4$ wherein m is 0 or 1 and $R_4$ is hydrogen atom or an alkyl group having 1 to 15 carbon atoms, and * means an asymmetric carbon atom. The liquid crystalline compound disclosed therein have a comparatively high melting point. It is also known that a liquid crystalline compound having a lower melting point can advantageously be incorporated in a larger amount in a liquid crystal composition.

SUMMARY DESCRIPTION OF THE INVENTION

Under the circumstances, the present inventors have intensively studied as to inhibition of free rotation of dipole moiety in the conventional ferroelectric liquid crystalline compounds and as to improvement of the above liquid crystalline compound (I) and have found that the free rotation can be inhibited by providing a compound wherein the asymmetric carbon atom is contained in a 5-membered lactone ring, by which there can be obtained a chemically stable liquid crystalline compound having ferroelectricity and that the introduction of a methyl group at the 2-position of the lactone ring lowers a melting point of the compound and it thereby can be incorporated into a liquid crystal composition in an increased amount without deteriorating the chemical stability and ferroelectricity of the composition.

An object of the invention is to provide a novel ferroelectric liquid crystalline compound which is chemically stable and is useful as an element for display devices or an element for opto-electronics devices. Another object of the invention is to provide liquid crystalline compounds having an optically active γ-lactone ring in the molecule wherein one or two asymmetric carbon atoms are present in the 5-membered lactone ring. A further object of the invention is to provide a liquid crystal composition containing at least one kind of the novel liquid crystalline compounds. A still further object of the invention is to provide an element for opto-electronics devices comprising the composition. These and other objects and advantages of the invention will be apparent to those skilled in the art from the following description.

DETAILED DESCRIPTION OF THE INVENTION

The novel liquid crystalline compounds of the invention are compounds having an optically active γ-lactone ring and having the following general formula (A):

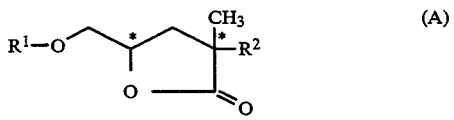

wherein $R^1$ is a group selected from the group consisting of

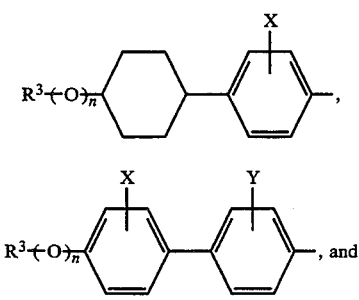

-continued

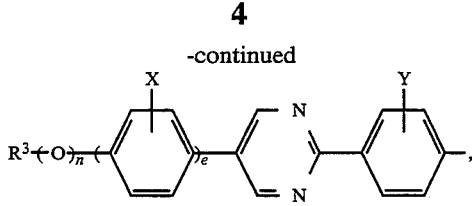

n and e are each independently 0 or 1, $R^3$ is an alkyl group having 1 to 15 carbon atoms or an alkenyl group having 2 to 15 carbon atoms, said alkyl and alkenyl groups having each optionally one or more asymmetric carbon atoms, X and Y are each hydrogen atom, a halogen atom or a cyano group, $R^2$ is an alkyl group having 1 to 15 carbon atoms or an alkenyl group having 2 to 15 carbon atoms, said alkyl and alkenyl groups having each optionally one or more asymmetric carbon atoms, and * means an asymmetric carbon atom.

In the specification, the term "alkyl group" for $R^2$ and $R^3$ includes methyl, ethyl, n-propyl, n-butyl, n-pentyl, n-hexyl, n-heptyl, n-octyl, n-nonyl, n-decyl, n-undecyl, n-dodecyl, n-tridecyl, n-tetradecyl, n-pentadecyl, isopropyl, t-butyl, 2-methylpropyl, 1-methylpropyl, 3-methylbutyl, 2-methylbutyl, 1-methylbutyl, 4-methylpentyl, 3-methylpentyl, 2-methylpentyl, 1-methylpentyl, 5-methylhexyl, 4-methylhexyl, 3-methylhexyl, 2-methylhexyl, 1-methylhexyl, 6-methylheptyl, 5-methylheptyl, 4-methylheptyl, 3-methylheptyl, 2-methylheptyl, 1-methylheptyl, 7-methyloctyl, 6-methyloctyl, 5-methyloctyl, 4-methyloctyl, 3-methyloctyl, 2-methyloctyl, 1-methyloctyl, 8-methylnonyl, 7-methylnonyl, 6-methylnonyl, 5-methylnonyl, 4-methylnonyl, 3-methylnonyl, 2-methylnonyl, 1-methylnonyl, 3,7-dimethyloctyl, 3,7,11-trimethyldodecyl, and the like.

The term "alkenyl" for $R^2$ and $R^3$ includes a linear alkenyl such as vinyl, propenyl, butenyl, pentenyl, hexenyl, heptenyl, octenyl, nonenyl, decenyl, undecenyl, dodecenyl, tridecenyl, tetradecenyl, pentadecenyl, etc. and a branched chain alkenyl such as 1-methylpropenyl, 2-methylpropenyl, 3-methylpropenyl, 4-methylpropenyl, etc.

The novel compounds of this invention contain a carbonyl group within a 5-membered ring and one or two asymmetric carbon atoms on the ring as a moiety having a dipole moment as an origin of ferroelectricity, and hence, the free rotation at this moiety is inhibited and thereby the dipole moiety is directed to one direction, which is effective for enlarging the spontaneous polarization and for increasing the response speed. Further, the substitution at the benzene ring of $R^1$ in the formula (A) with a halogen atom or a cyano group allows lowering a melting point of the compound of the invention, broadening the temperature range of the chiral smectic C (SmC*) phase at the lower temperature side, enlarging a chilt angle and increasing a spontaneous polarization. In addition, the introduction of a cyano group is advantageous in that it provides a compound having a large negative anisotropy of the dielectric constant which is necessary for effectively driving the ferroelectric liquid crystal.

In the liquid crystalline compounds (A) of this invention, when $R^2$ is methyl group, only one asymmetric carbon atom is contained, but when $R^2$ is a group other than a methyl group, two asymmetric carbon atoms are contained in the γ-lactone ring and hence there are present two kinds of diastereomer. These are all suitable for inhibition of free rotation of the dipole moiety, and they are used as a liquid crystal alone or in a mixture of two or more thereof.

The compounds (A) of the invention can be prepared by a process which comprises reacting an optically active γ-lactone compound of the general formula (B):

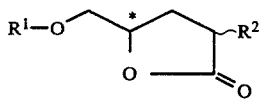

wherein $R^1$, $R^2$ and the symbol * are the same as $R^1$, $R^2$ and * in the formula (A), with a methyl halide (e.g. CH$_3$I) under basic conditions. That is, the compound of the formula (B) is reacted with 1 to 1.5 equivalents of a base to give an enolate anion of the compound (B), which is then reacted with 1 to 1.5 equivalents of a methyl halide. The base used therein includes lithium diisopropylamide, sodium diisopropylamide, potassium diisopropylamide, lithium 1,1,1,3,3,3-hexamethyldisilazide, sodium 1,1,1,3,3,3-hexamethyldisilazide, potassium 1,1,1,3,3,3-hexamethyldisilazide, lithium 1,1,1,3,3,3-hexaethyldisilazide, sodium 1,1,1,3,3,3-hexaethyldisilazide, potassium 1,1,1,3,3,3-hexaethyldisilazide, potassium t-butoxide, and the like.

The above reaction is carried out in an organic solvent. The organic solvent is preferably t-butyl alcohol when the base is potassium t-butoxide. When the base is other than potassium t-butoxide, the organic solvent is preferably ethers such as tetrahydrofuran, ethyl ether, dimethoxyethane, diethyleneglycol dimethyl ether, dioxane, etc.; aprotic solvents such as dimethylformamide, dimethyl sulfoxide, dimethylacetamide, hexamethylphosphoric triamide, etc.; or a mixed solvent thereof.

The reaction is usually carried out at the reaction temperature of 30° to 90° C. for 15 minutes to 5 hours when the base is potassium t-butoxide. In case a base other than potassium t-butoxide is employed, the reaction is usually carried out at −80° to 30° C. and completes immediately or within at least 2 hours although the reaction temperature may vary depending on the kind of the base used therein.

The starting compound (B) can be prepared by reacting an optically active glycidyl ether of the general formula (C):

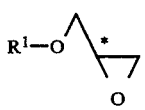

wherein $R^1$ and * are the same as $R^1$ and * in the formula (A), with a ketoester derivative of malonate a of the general formula (D):

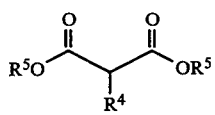

wherein $R^4$ is hydrogen atom or an alkyl group having 1 to 15 carbon atoms and $R^5$ is a lower alkyl group having 1 to 4 carbon atoms, in the presence of a base in an organic solvent. That is, the compound (B) can be prepared by reacting under reflux the compound (C) with 1 to 5 equivalents of the compound (D) in the presence of 1 to 5 equivalents of a base in an organic solvent for 1.5 to 24 hours. The base used therein includes alkali metal alkoxides (e.g. sodium methoxide, sodium ethoxide, potassium t-butoxide, etc.), alkali metal hydrides (e.g. sodium hydride, lithium hydride, etc.), and alkyl alkali metals (e.g. n-butyllithium, etc.), and the organic solvent includes alcohols (e.g. methanol, ethanol, t-butyl alcohol, etc.), ethers (e.g. tetrahydrofuran, diethyl ether, dimethoxyethane, diethylene glycol dimethyl ether, dioxane, etc.), aprotic polar solvents (e.g. dimethylformamide, dimethylsulfoxide, hexamethylphosphoric triamide, etc.), and a mixture of these solvents.

The starting optically active glycidyl ether (C) can be prepared by a process as shown in the following reaction scheme:

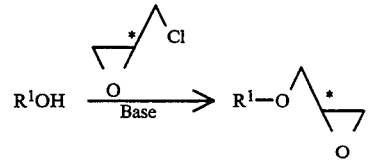

wherein $R^1$ and the symbol * are the same as $R^1$ and * in the formula (A).

That is, a phenol derivative of the formula $R^1$OH is reacted with an optically active epichlorohydrin in the presence of a base. The optically active epichlorohydrin is preferably used in an amount of 1 to 10 equivalents to the phenol derivative, and the base is preferably used in an amount of 1 to 5 equivalents to the phenol derivative. The base includes alkali metal hydroxides or alkoxides, such as sodium hydroxide, potassium hydroxide, potassium t-butoxide, and the like. The above reaction may proceed smoothly without any catalyst, but may be carried out in the presence of a catalyst. The catalyst includes quaternary ammonium halides, such as benzyltriethylammonium chloride, benzyltriethylammonium bromide, benzyltrimethylammonium chloride, benzyltrimethylammonium bromide, etc. and is used in an amount of 0.01 to 0.1 equivalent to the phenol derivative. An excess amount of the optically active epichlorohydrin may be used as the solvent, but there is preferably used a suitable polar solvent such as dimethylformamide, dimethylsulfoxide, dimethylacetamide, acetonitrile, t-butyl alcohol, and water. The reaction is usually carried out at a temperature of 50° to 80° C. for 0.5 to 3 hours.

Alternatively, the optically active glycidyl ether (C) may also be prepared by reacting the phenol derivative of the formula $R^1$OH with an optically active epichlorohydrin in the presence of an amine (e.g. morpholine, piperidine, pyridine, etc.) of 0.1 to 0.5 equivalent to the phenol derivative and subjecting the resulting optically active chlorohydrin derivative to cyclization reaction with 1 to 5 equivalents of a base, such as an alkali metal hydroxide, carbonate or alkoxide (e.g. sodium hydroxide, potassium hydroxide, potassium carbonate, sodium carbonate, potassium t-butoxide, etc.). The latter process is carried out in two steps but is advantageous in that the extraction of the product can easily be done. This reaction is usually carried out at a temperature of 50° to 80° C. for 3 to 24 hours.

When a racemic epichlorohydrin is used in the above reaction, there is obtained a glycidyl ether in the form of a racemic mixture. The starting optically active epichlorohydrin can be prepared in a high purity by the processes as described in Japanese Patent First Publication (Kokai) Nos. 132196/1986 and 6697/1987 (as to R isomer) and by the process as described in Japanese Patent Application No. 283393/1987 (as to S isomer).

Besides, the starting phenol derivative used for the preparation of the compound (C) can be prepared by the processes as shown in the following Reaction Schemes-I to -XI, wherein $R^3$ is the same as $R^3$ in the formula (A), $R^{3'}$ is an alkyl group having a carbon atom one smaller than that in $R^3$, X is a halogen atom, Ph in Reaction Scheme-VI means phenyl, R' in Reaction Scheme-VI is a lower alkyl group having 1 to 4 carbon atoms and Ts in Reaction Scheme-X means p-toluenesulfonyl group.

That is, 4-(4-trans-alkylcyclohexyl)phenols, 4-(4-alkyloxyphenyl)phenols, and 4-(4-alkylphenyl)phenols are prepared by the known processes as shown in Reaction Schemes-I, -II and -III, respectively.

Reaction Scheme-III

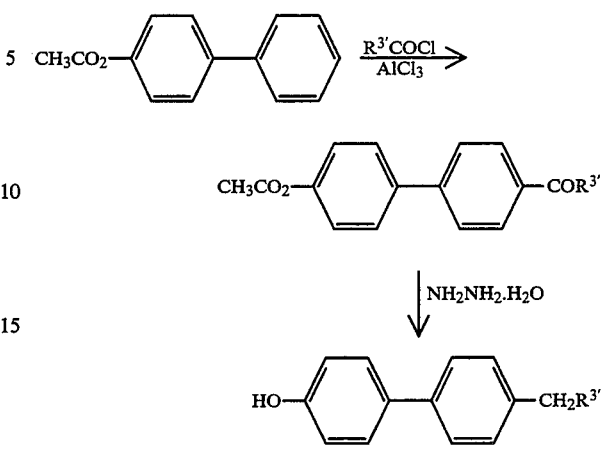

Besides, 4-(5-alkyl-2-pyrimidinyl)phenols and 4-(5-alkyloxy-2-pyrimidinyl)phenols are prepared by the Reaction Scheme-I

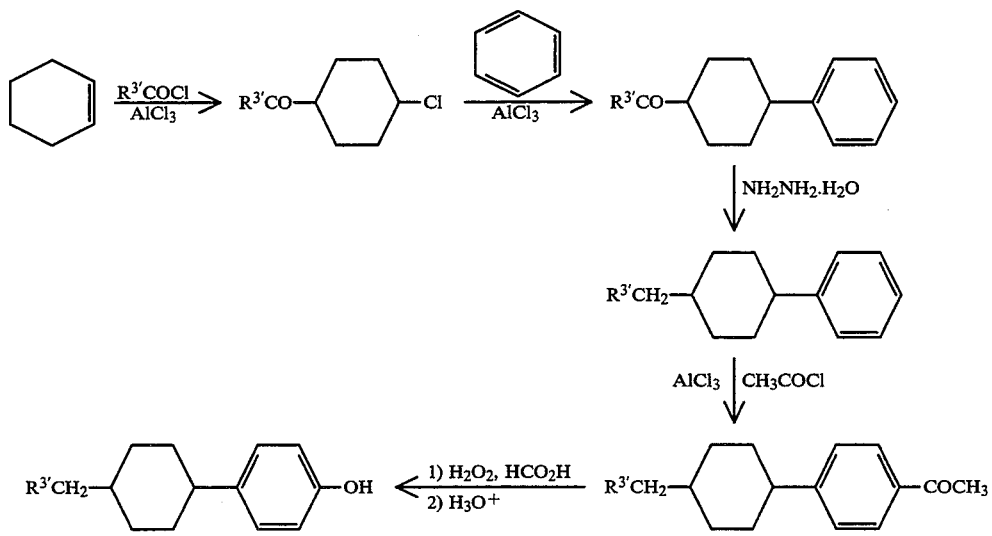

Reaction Scheme-II

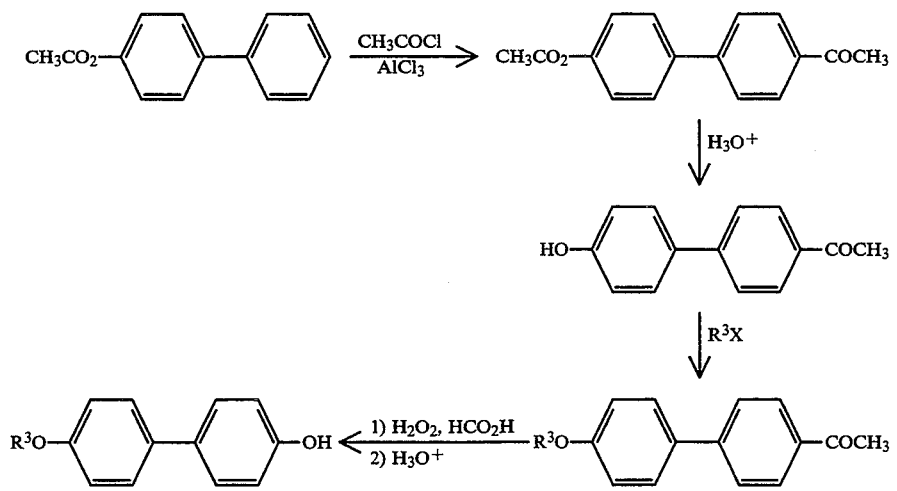

processes as shown in the following Reaction Schemes-IV and -V, respectively, which are disclosed in Japanese Patent First Publication (Kokai) Nos. 189274/1986 and DE 144,409.
Moreover, 4-[5-(4-alkyloxyphenyl)-2-pyrimidinyl]-phenols and 4-[5-(4-alkylphenyl)-2-pyrimidinyl]phenols are prepared by the processes as shown in the following Reaction Scheme-VI.
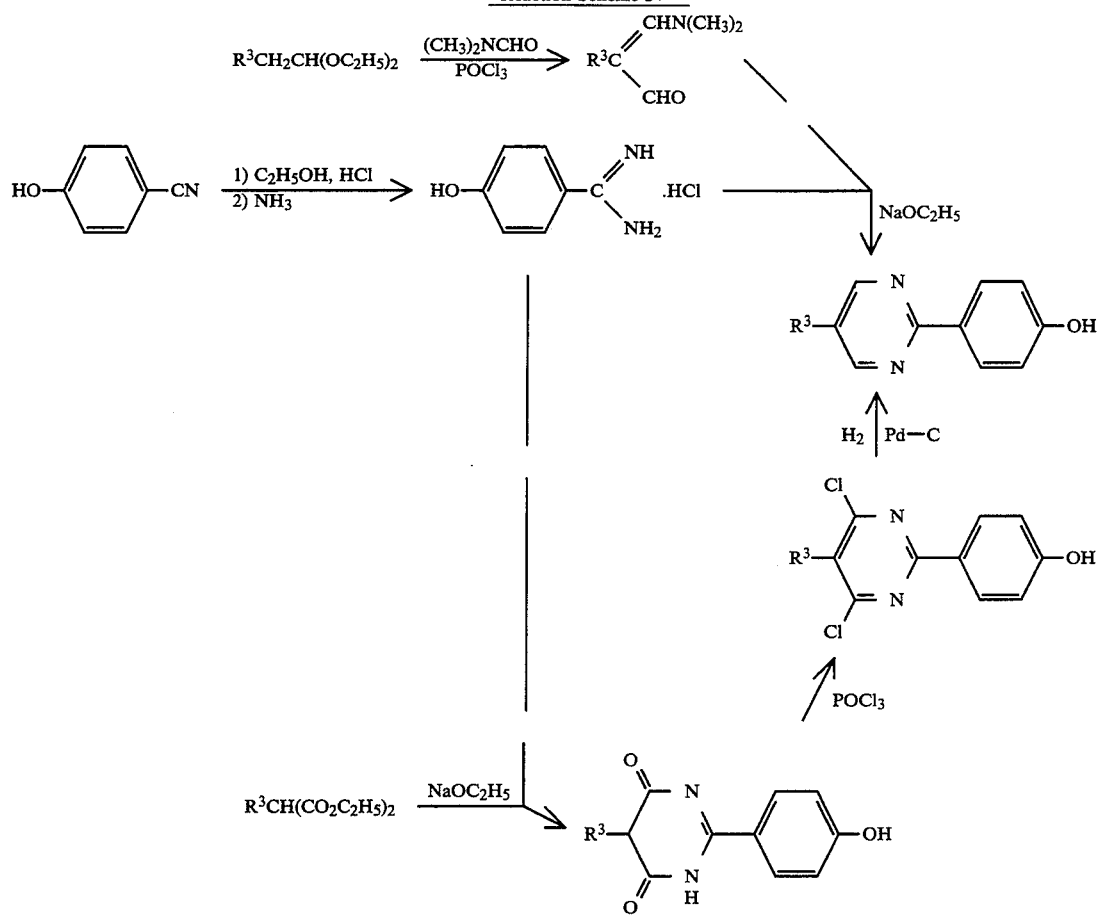
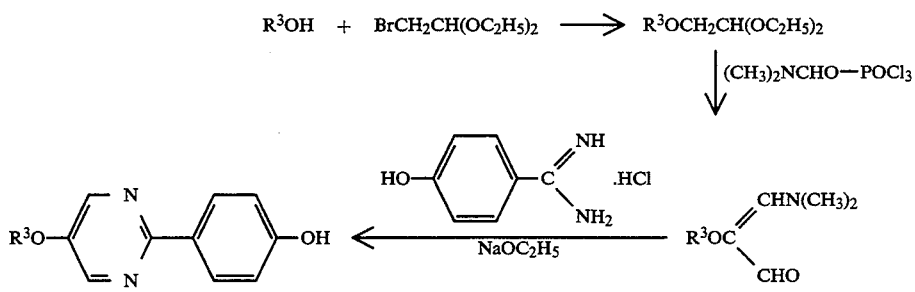
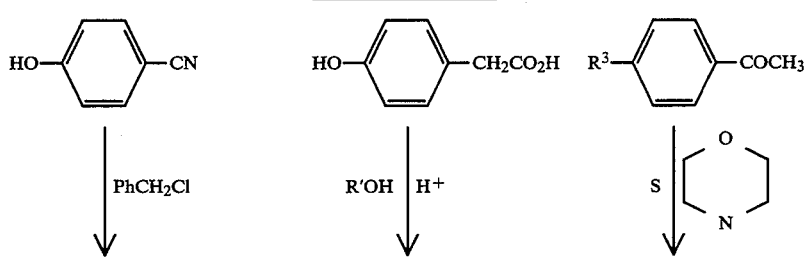

-continued
Reaction Scheme-VI

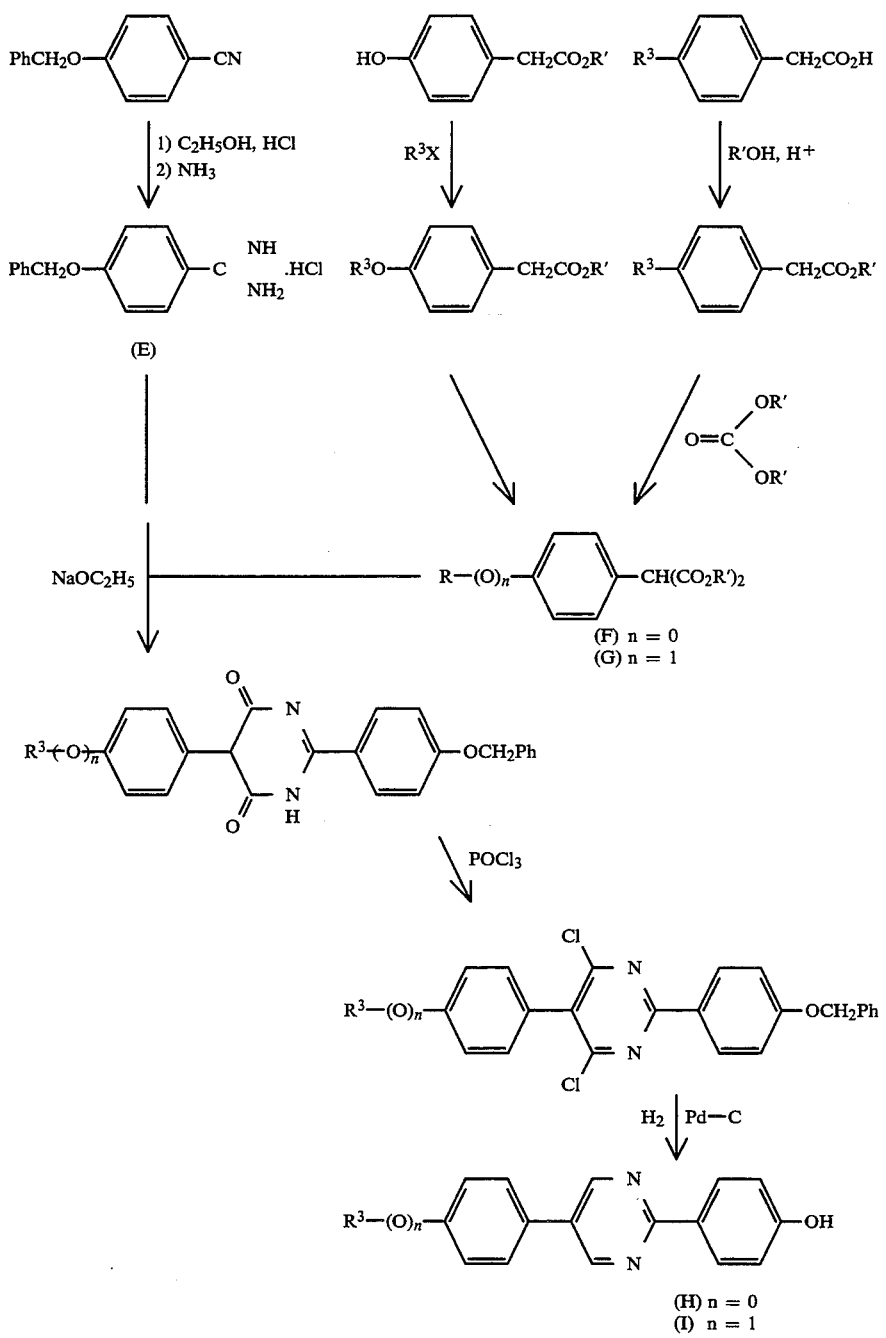

(H) n = 0
(I) n = 1

According to the process of Reaction Scheme-VI, Compound (E) is prepared by protecting the hydroxy group of p-hydroxybenzonitrile with a benzyl group and converting the cyano group thereof into amidine hydrochloride in a usual manner. Separately, p-hydroxyphenylacetic acid is esterified with a lower alcohol, and the phenolic hydroxy group is alkylated with an alkyl halide, alkyl p-toluenesulfonate or alkyl methanesulfonate, followed by reacting with diethyl carbonate in the presence of a base to give diethyl malonate derivative (G).

The amidine hydrochloride (E) is condensed with the diethyl malonate derivative (G) in the presence of a base such as alkali metal alkoxides (e.g. sodium ethoxide, sodium methoxide, etc.), followed by reacting with phosphorus oxychloride in the presence of a base such as organic amines (e.g. N,N-diethylaniline, pyridine, 4-(N,N-dimethylamino)pyridine, etc.), and the resulting compound is reduced with hydrogen gas in the presence of Pd-C catalyst to give the desired 4-[5-(4-alkyloxyphenyl)-2-pyrimidinyl]phenol (I).

In the above process, when a diethyl p-alkylphenylmalonate (F) is used instead of the diethyl malonate derivative (G) and the compound (E) and the compound (F) are reacted like in the reaction of the compound (E) and the compound (G), there is prepared 4-[5-(4-alkylphenyl)-2-pyrimidinyl]phenol (H).

The diethyl p-alkylphenylmalonate (F) can be prepared by subjecting a p-alkylacetophenone to a Willgerodt reaction, esterifying the resulting phenylacetic acid derivative with a lower alcohol, and condensing the resultant with diethyl carbonate.

The starting phenol derivative wherein the benzene ring has a substituent of a halogen atom or a cyano group can be prepared by conventional processes as shown in the following Reaction Schemes-VII to XI.

-continued
Reaction Scheme-VIII

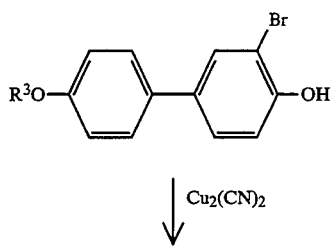

Reaction Scheme-VII

Preparation of 4-(4-alkylphenl)-2-halogenophenol and 4-(4-alkylphenol)-2-cyanophenol:

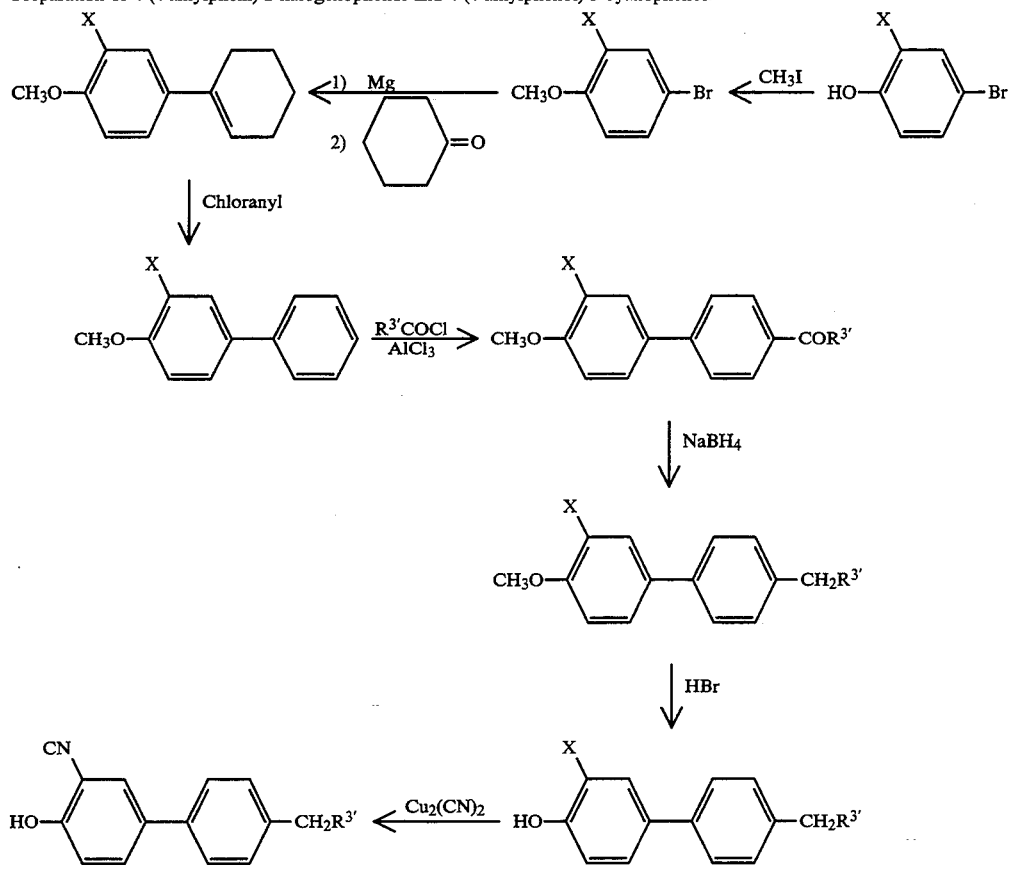

Reaction Scheme-VIII

Preparation of 4-(4-alkoxyphenyl)-2-halogenophenol and 4-(4-alkoxyphenyl)-2-cyanophenol (Japanese Patent First Publication No. 166646/1985):

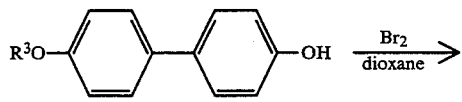

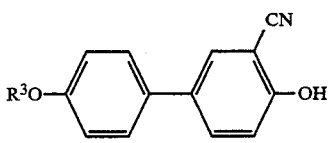

Reaction Scheme-IX

Preparation of 4-(4-alkoxy-3-fluorophenyl)phenol (The 12th Liquid Crystal Meeting, 2 F18):

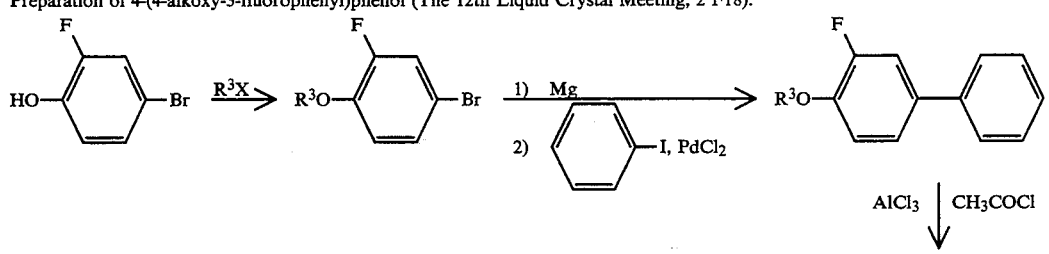

-continued
Reaction Scheme-IX

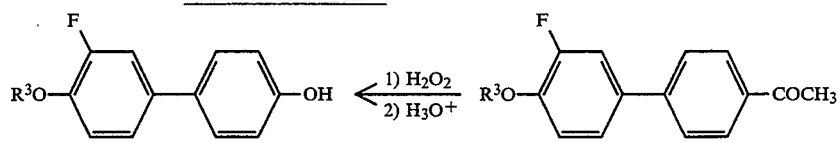

Reaction Scheme-X
Preparation of 4-(4-alkoxy-3-bromophenyl)phenol and 4-(4-alkoxy-3-cyanophenyl)phenol
(Japanese Patent First Publication No. 166646/1985):

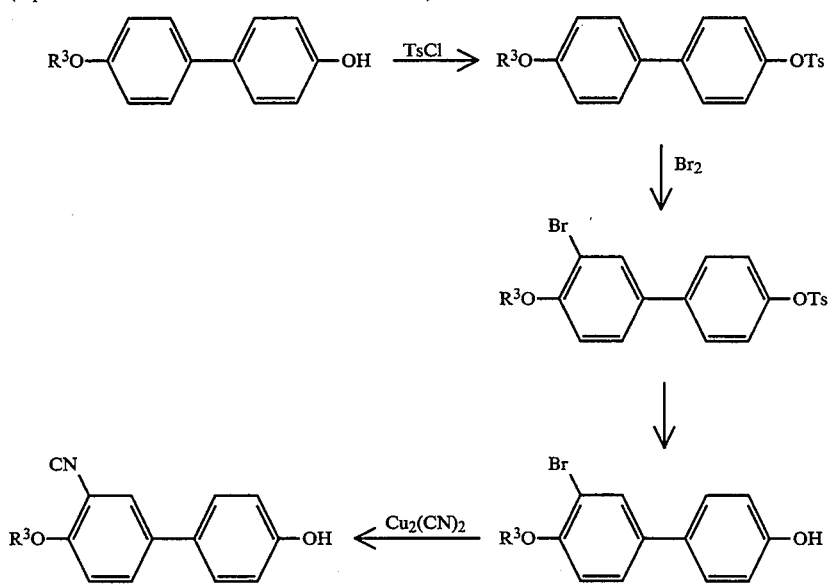

Reaction Scheme-XI
Preparation of 4-(5-alkyl-2-pyrimidinyl)-2-halogenophenol and
4-(5-alkyl-2-pyrimidinyl)-2-cyanophenol (The 13th Liquid Crystal Meeting 1Z 06):

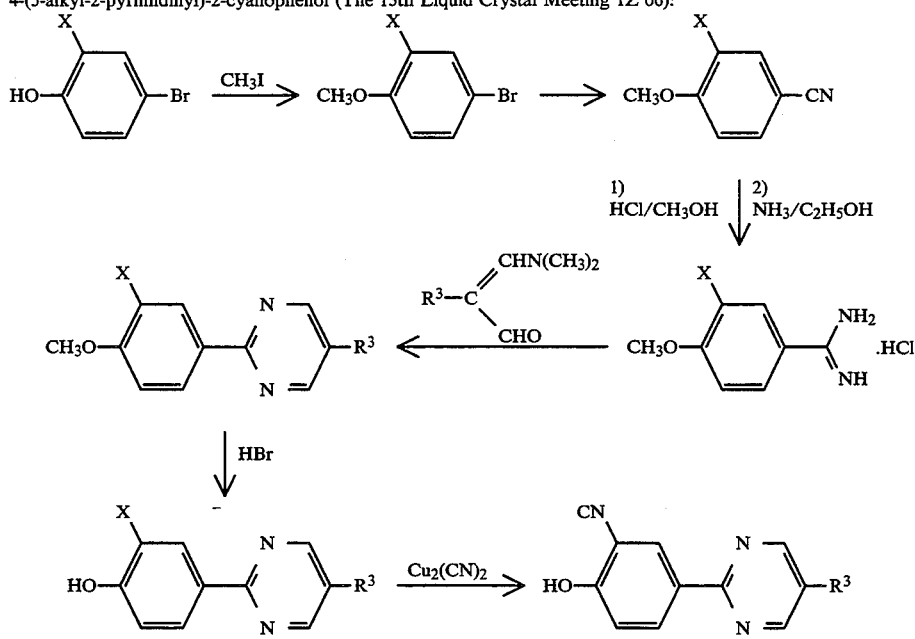

The liquid crystal composition of this invention may be obtained by mixing at least one compound (A) as prepared above with a chiral or non-chiral liquid crystal or a mixture thereof.

The chiral or non-chiral liquid crystal employed in the liquid crystal composition of this invention is not particularly limited but may be any conventional chiral or non-chiral liquid crystal which shows chiral smectic C phase after mixing with the compound (A).

The conventional liquid crystal includes those described in e.g. Flüssige Kristalle in Tabellen I, VEB Deutscher Verlag für Grundstoffindustrie, Leipzig, 1974; Flüssige Kristalle in Tabellen II, VEB Deutscher Verlag für Grundstoffindustrie, Leipzig, 1984.

Typical example of the above chiral or non-chiral liquid crystal includes the compound of the general formula (J):

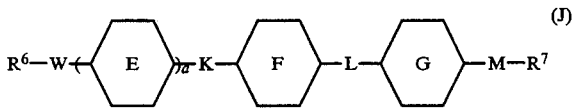

wherein E, F and G are each independently a 6-membered ring selected from the group consisting of:

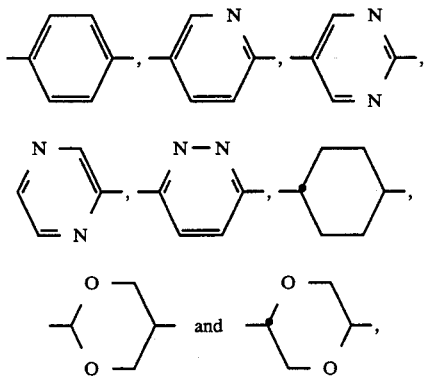

the hydrogen atom(s) in the 6-membered ring being optionally substituted with a halogen atom, cyano group or nitro group; a is 0 or 1; W, K, L and M are each a single bond or a group selected from the group consisting of

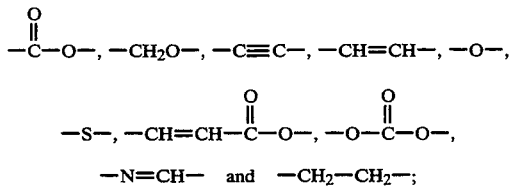

—N=CH— and —CH$_2$—CH$_2$—;

provided that K is a single bond when a=0; $R^6$ and $R^7$ are each independently a straight chain or branched chain alkyl group having 1 to 15 carbon atoms, which may contain one or more asymmetric carbon atoms.

Particularly suitable examples of the chiral or non-chiral liquid crystal are a compound of the formula (J-1):

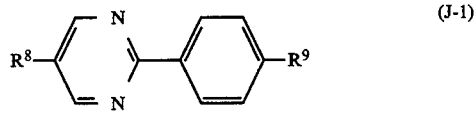

wherein $R^8$ and $R^9$ are the same or different and are each a straight chain or branched chain alkyl group having 1 to 15 carbon atoms or a straight chain or branched chain alkoxy group having 1 to 15 carbon atoms, said alkyl and alkoxy groups having optionally one or more asymmetric carbon atoms, and a compound of the formula (J-2):

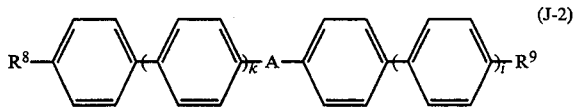

wherein $R^8$ and $R^9$ are as defined above, A is

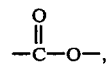

and k and i are independently 0 or 1, but k+i≠2.

The liquid crytal composition of the invention comprises preferably one part by weight of a compound of the formula (A) and 3 to 999 parts by weight of a compound of the formula (J).

The liquid crystal composition of this invention is useful for preparing a liquid crystal cell of an electrically controlled birefrigence mode or guest-host mode, which is prepared by attaching a transparent electrode to the liquid crystal composition of this invention, sandwiching the resultant electrode-attached liquid crystal composition with two sheets of glass plate which is surface-treated for orientation with a polymer (e.g. polyethylene, polyester, nylon, polyvinyl alcohol, polyimide, etc.), and providing a polarizer. The liquid crystalline compounds (A) and the racemic compounds of this invention may be added to other optically active liquid crystalline compounds in order to regulate the helical pitch thereof.

The liquid crystalline compounds of this invention have excellent heat stability and light stability, and the optically active compounds have excellent properties as ferroelectric liquid crystal. The liquid crystalline compounds of this invention are also useful for the following utilities.

(1) Additives for TN (Twisted Nematic) type or STN (Super Twisted Nematic) type liquid crystals in order to inhibit occurrence of reverse domain.

(2) Display element utilizing cholesteric-nematic phase transfer effects (cf. J. J. Wysoki, A. Adams and W. Haas; Phys. Rev. Lett., 20, 1024, 1968).

(3) Display element utilizing White-Taylor type guest host effects (cf. D. L. White and G. N. Taylor; J. Appl. Phys., 45, 4718, 1974).

(4) Notch filter or band-pass filter utilizing selective scattering effects by fixing the cholesteric phase in matrix (cf. F. J. Kahn; Appl. Phys. Lett., 18, 231, 1971).

(5) Circularly polarized light beam splitter utilizing circularly polarized light characteristics of the cholesteric phase (cf. S. D. Jacob; SPIE. 37, 98, 1981).

This invention is illustrated by the following Preparations and Examples, but should not be construed to be limited thereto.

In Examples, the positions of R and S in the optically active compounds (A) of this invention are shown by the position numbers in the following formula:

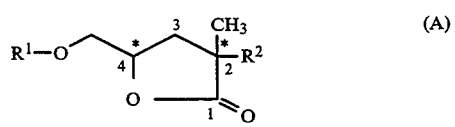

The phase transfer temperature in Examples was measured by DSC (Differential Scanning Colorimetry) and a polarizing microscope. Besides, the symbols in the phase transfer temperature mean:

C: Crystalline phase
SmA: Smectic A phase
SmC: Smectic C phase
SmC*: Chiral smectic C phase
SmI: Non-identified smectic phase other than SmA, SmC and SmC*.
N: Nematic phase
N*: Chiral nematic phase
I: Isotropic liquid The chiral smectic C phase (SmC*) was further confirmed by measuring dielectric constant thereof.

PREPARATION OF PHENOL DERIVATIVES

Preparation 1

Preparation of 4-[5-(4-n-octyloxyphenyl)-2pyrimidinyl]phenol i) Preparation of 4-benzyloxyphenylamidine hydrochloride:

4-Cyanophenol (95.2 g), benzyl chloride (127 g) and potassium carbonate (138 g) are refluxed in acetone (160 ml) for 5 hours. The product is separated by filtration, concentrated under reduced pressure, and thereto is added benzene. The mixture is washed with water, and benzene is distilled off under reduced pressure to give 4-benzyloxybenzonitrile (141.38 g). The 4-benzyloxybenzonitrile (141 g) is dissolved in benzene (338 ml) and thereto is added ethanol (270 ml), and the mixture is cooled to 0° C. Into the resulting slurry is bubbled hydrogen chloride gas (36 liters) with stirring, and thereafter, the temperature is raised to 25° C., and the mixture is allowed to stand for 2 days. The reaction mixture is concentrated under reduced pressure until ⅓ volume, and to the concentrated mixture is added ether. The precipitated crystals are separated by suction filtration to give an imide ester (183 g).

The above-obtained imide ester (183 g) is mixed with ethanol (270 ml) to give a slurry, and thereto is added a solution of ammonia (60.75 g) in ethanol (405 ml). After allowing the mixture to stand at room temperature for 2 days, the solvent is distilled off under reduced pressure to give 4-benzyloxyphenylamidine hydrochloride (164.5 g).

NMR (DMSO-d$_6$) δ: 5.19 (2H, s), 7.17 (2H, d, J=9.0 Hz), 7.35 (5H, s), 7.86 (2H, d).

ii) Preparation of diethyl 4-n-octyloxyphenylmalonate:

4-Hydroxyphenylacetic acid (50.0 g) is dissolved in ethanol (400 ml) and thereto is added conc. sulfuric acid (0.5 ml). The mixture is refluxed with stirring, and ethanol is distilled off to give ethyl 4-hydroxyphenylacetate (60 g).

The ethyl 4-hydroxyphenylacetate (59 g) and sodium ethoxide (22.4 g) are dissolved in ethanol (150 ml) and thereto is added n-octyl bromide (63.5 g), and the mixture is refluxed for 3 hours and concentrated under reduced pressure, and thereto is added ethyl acetate to dissolve the oily substance. The mixture is washed with water, dried over anhydrous magnesium sulfate, distilled under reduced pressure to remove ethyl acetate, and further distilled under reduced pressure to give ethyl 4-n-octyloxyphenylacetate (79.6 g, b.p. 179° C./0.1 mmHg).

The obtained ethyl 4-n-octyloxyphenylacetate (79 g), ethanol (140 ml), diethyl carbonate (300 ml) and sodium ethoxide (19.3 g) are mixed, and the mixture is heated with stirring while ethanol is distilling off. The reaction mixture is transferred into ice water and is acidified with hydrochloric acid. The organic layer is separated and the solvent is distilled off to give diethyl 4-n-octyloxyphenylmalonate (91.6 g).

NMR (CDCl$_3$) δ: 0.5–2.0 (21H, m), 3.90 (2H, t, J=6.0 Hz), 4.16 (4H, q, J=7.2 Hz), 4.52 (1H, s), 6.80 (2H, d, J=9.0 Hz), 7.26 (2H, d, J=9.0 Hz).

iii) Preparation of 4-[5-(4-n-octyloxyphenyl)-2-pyrimidinyl]phenol:

4-Benzyloxyphenylamidine hydrochloride (65.6 g) and diethyl 4-n-octyloxyphenylmalonate (91.0 g) are dissolved in methanol (500 ml) and thereto is added sodium methoxide (44.8 g), and the mixture is refluxed with stirring for 9 hours. After cooling, the reaction mixture is acidified with sulfuric acid, and the precipitated crystals are separated by suction filtration to give yellow crystals (77.7 g).

The above yellow crystals (77 g), phosphorus oxychloride (310 ml) and N,N-diethylaniline (46.5 ml) are mixed and refluxed with stirring for 26 hours. The excess phosphorus oxychloride is distilled off under reduced pressure, and the residue is transferred into ice-water and extracted with ether. The extract is washed with water and distilled to remove ether to give a crude product (70 g). The product is recrystallized from ether to give a compound (21 g) of the following formula:

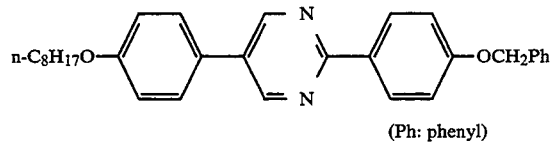

(Ph: phenyl)

NMR (CDCl$_3$) δ: 0.4–2.1 (15H, m), 3.99 (2H, t, J=6.0 Hz), 5.09 (2H, s), 6.7–7.5 (11H, m), 8.38 (2H, d, J=9.0 Hz).

The colorless crystals obtained above (19.8 g), ethanol (757 ml), magnesium oxide (11.4 g), water (57 ml) and 10% Pd-C (4 g) are heated with stirring at 60° C. under hydrogen atmosphere until a theoretical amount of hydrogen is absorbed. The reaction mixture is filtered with suction, and the filtrate is concentrated to give the desired 4-[5-(4-n-octyloxyphenyl)-2-pyrimidinyl]phenol (7.7 g), m.p. 137° C.

NMR (CDCl$_3$) δ: 0.5–2.1 (15H, m), 4.00 (2H, t, J=6.0 Hz), 6.92 (2H, d, J=9.0 Hz), 7.01 (2H, d, J=9.0 Hz), 7.50 (2H, d, J=9.0 Hz), 8.30 (2H, d, J=9.0 Hz), 8.94 (2H, s).

PREPARATION OF THE COMPOUNDS (C)

Preparation 2

The starting phenol derivative (2.50 g) of the following formula:

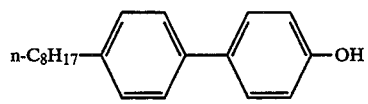

and R-(—)-epichlorohydrin (chemical purity: 98.5% or more, optical purity: 99% or more, 4.25 g) and benzyltriethylammonium chloride (20 mg) are dissolved in dimethylformamide (3 ml) and thereto is added dropwise 24 wt. % aqueous sodium hydroxide (1.2 equivalent) at 60° C. After reacting at the same temperature for 40 minutes, the reaction mixture is cooled to room temperature and extracted with ether. The extract is distilled under reduced pressure to remove the solvent. The residue is purified by silica gel chromatography to give S isomer of glycidyl ether (1.62 g) of the following formula:

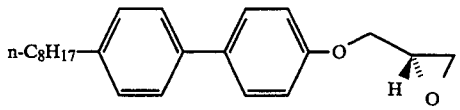

m.p. 90° C.
$[\alpha]_D^{25} = +4.44°$ (c=1.01, CH$_2$Cl$_2$)
NMR (CDCl$_3$) δ: 0.50–3.00 (19H, m), 3.10–3.50 (1H, m), 3.80–4.30 (2H, m), 6.75–7.60 (8H, m).

Preparation 3

The starting phenol derivative (5.28 g) of the following formula: -

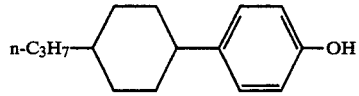

and S-(−)-epichlorohydrin (chemical purity: 98.5% or more, optical purity: 99% or more, 11.55 g), potassium t-butoxide (3.00 g) and t-butyl alcohol (45 ml) are mixed and the mixture is stirred at 60° C. for 3 hours. The reaction mixture is distilled under reduced pressure to remove the solvent and the residue is extracted with chloroform. The extract is distilled under reduced pressure to remove the solvent. The residue is purified by silica gel chromatography to give the R isomer of the glycidyl ether (5.82 g) of the following formula:

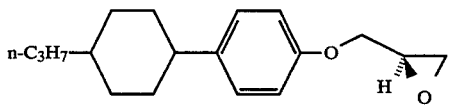

$[\alpha]_D^{31} = -5.71°$ (c=1.66, CH$_2$Cl$_2$)
NMR (CDCl$_3$) δ: 0.60–2.50 (17H, m), 2.60–2.95 (2H, m), 3.15–3.60 (1H, m), 3.80–4.30 (2H, m), 6.76 (2H, d, J=8.4Hz), 7.07 (2H, d, J=8.4Hz).

Preparation 4

A mixture of the starting phenol derivative (10 g) of the following formula:

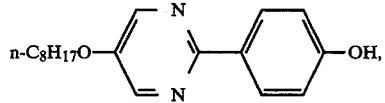

the same R-(−)-epichlorohydrin (16.07 g) as used in Preparation 2, 20 wt. % aqueous sodium hydroxide (7.33 g) and dimethylformamide (20 ml) is heated with stirring at 60°–70° C. for one hour. The reaction mixture is cooled and thereto is added water. The mixture is extracted with chloroform to obtain a crude product (11.67 g). The crude product is purified by silica gel chromatography to give the S isomer of the glycidyl ether (9.07 g) of the following formula:

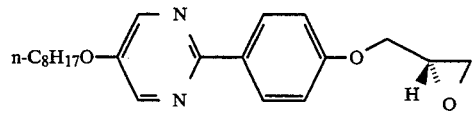

m.p. 74° C.
$[\alpha]_D^{24} = +1.66°$ (c=1.02, CH$_2$Cl$_2$)
NMR (CDCl$_3$) δ: 0.5–2.2 (15H, m), 2.6–3.0 (2H, m), 3.1–3.7 (1H, m), 3.8–4.4 (4H, m), 6.95 (2H, d, J=9.0 Hz), 8.26 (2H, d, J=9.0 Hz), 8.36 (2H, s).

Preparation 5

A mixture of the starting phenol derivative (7.44 g) of the following formula:

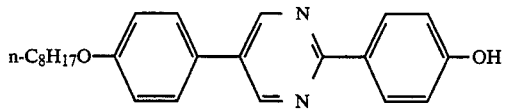

as prepared in Preparation 1, the same R-(−)-epichlorohydrin (9.16 g) as used in Preparation 2, 50 wt. % aqueous sodium hydroxide (1.74 g) and dimethylformamide (77 ml) is stirred at 60°–70° C. for 3 hours. The reaction mixture is cooled and thereto is added water, and the mixture is extracted with dichloromethane. The extracted product is purified by silica gel chromatography to give the S isomer of the glycidyl ether (6.90 g) of the following formula:

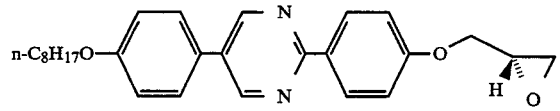

m.p. 198° C.
$[\alpha]_D^{25} = +0.95°$ (c=1.04, CH$_2$Cl$_2$)
NMR (CDCl$_3$) δ: 0.6–2.1 (15H, m), 2.6–3.0 (2H, m), 3.2–3.5 (1H, m), 3.8–4.5 (2H, m), 6.99 (4H, d, J=9.0 Hz), 7.50 (2H, d, J=9.0 Hz), 8.40 (2H, d, J=9.0 Hz), 8.90 (2H, s).

PREPARATION OF THE COMPOUNDS (B)

Preparation 6

The optically active glycidyl ether prepared in Preparation 3, i.e. (R)-2,3-epoxypropyl 4-(trans-4-n-propylcyclohexyl)phenyl ether (406 mg), potassium t-butoxide (181 mg), dimethyl n-nonylmalonate (666 mg) and t-butyl alcohol (3 ml) are mixed, and the mixture is refluxed with stirring for 2 hours. The reaction mixture is cooled to room temperature and thereto is added dropwise 4N hydrochloric acid until pH 1. The mixture is then extracted three times with chloroform, and the extract is washed once with saturated saline solution and distilled under reduced pressure to remove the solvent. The residue is purified by silica gel chromatography to give γ-lactone derivatives, (2R, 4R) isomer (79 mg) and (2S, 4R) isomer (153 mg) of the following formulae:
(2R, 4R) isomer:

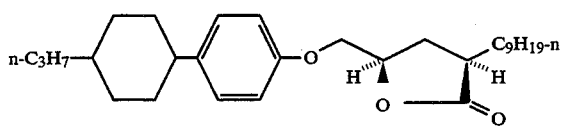

Phase transfer temperature:

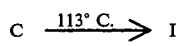

$[\alpha]_D^{32} = -31.45°$ (c=1.43, CH$_2$Cl$_2$)
NMR (CDCl$_3$) δ: 0.6–3.0 (39H, m), 4.0–4.2 (2H, m), 4.4–4.95 (1H, m), 6.76 (2H, d, J=8.0 Hz), 7.10 (2H, d, J=8.0 Hz)
IR (KBr): 1762 cm$^{-1}$.

(2S, 4R) isomer:

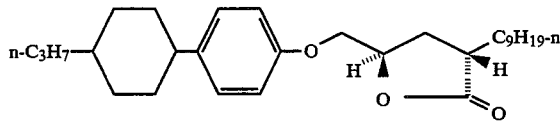

Phase transfer temperature:

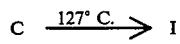

$[\alpha]_D^{28} = -27.82°$ (c=1.03, CH$_2$Cl$_2$)
NMR (CDCl$_3$) δ: 0.65–3.0 (39H, m), 4.0–4.2 (2H, m), 4.6–5.0 (1H, m), 6.76 (2H, d, J=8.0 Hz), 7.10 (2H, d, J=8.0 Hz)
IR (KBr): 1762 cm$^{-1}$.

Preparation 7

The S isomer of glycidyl ether prepared in Preparation 2 (370 mg), diethyl n-propylmalonate (442 mg), potassium t-butoxide (134 mg) and t-butyl alcohol (3 ml) are mixed, and the mixture is refluxed with stirring for 10 hours. The reaction mixture is cooled to room temperature and thereto is added dropwise 4N hydrochloric acid until pH 1. The mixture is washed with water and methanol to give white crystals. The product is separated and purified by silica gel chromatography to give γ-lactone derivatives, (2S, 4S) isomer (240 mg) and (2R, 4S) isomer (140 mg) of the following formulae:

(2S, 4S) isomer:

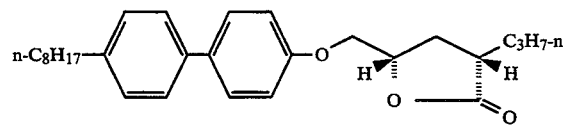

Phase transfer temperature:

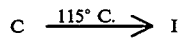

$[\alpha]_D^{26} = +32.67°$ (c=1.081, CH$_2$Cl$_2$)
NMR (CDCl$_3$) δ: 0.70–3.00 (27H, m), 4.00–4.25 (2H, m), 4.40–4.85 (1H, m), 6.60–7.60 (8H, m)
IR (KBr): 1762 cm$^{-1}$.

(2R, 4S) isomer:

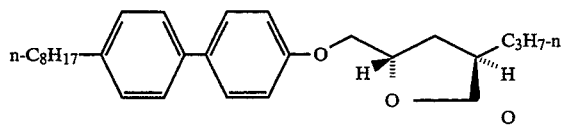

Phase transfer temperature:

$[\alpha]_D^{26} = +22.50°$ (c=0.504, CH$_2$Cl$_2$)
NMR (CDCl$_3$) δ: 0.70–3.00 (27H, m), 4.00–4.25 (2H, m), 4.50–5.00 (1H, m), 6.60–7.60 (8H, m)
IR (KBr): 1762 cm$^{-1}$.

Preparation 8

The S isomer of glycidyl ether prepared in Preparation 5 (518 mg), dimethyl n-pentylmalonate (940 mg) and potassium t-butoxide (269 mg) are dissolved in dimethylformamide (5 ml) and t-butyl alcohol (5 ml), and the mixture is heated with stirring at 90° C. for 5 hours. After the reaction, the reaction mixture is treated in the same manner as described in Preparation 7 to give γ-lactone derivatives (690 mg) of the following formulae. The product is a mixture of diastereomers and is purified by silica gel chromatography to give (2S, 4S) isomer and (2R, 4S) isomer.

(2S, 4S) isomer:

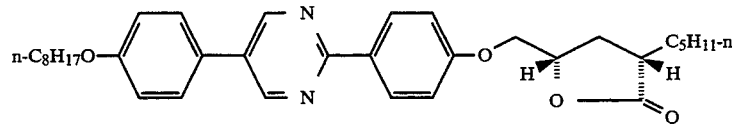

Phase transfer temperature:

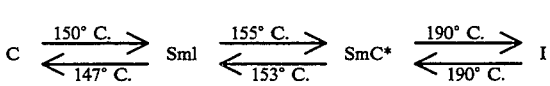

NMR (CDCl$_3$) δ: 0.4–3.0 (29H, m), 3.7–4.3 (4H, m), 4.71 (1H, m), 7.00 (4H, d, J=9.0 Hz), 7.50 (2H, d, J=9.0 Hz), 8.39 (2H, d, J=9.0 Hz), 8.89 (2H, s)
IR (nujol): 1778 cm$^{-1}$.

(2R, 4S) isomer:

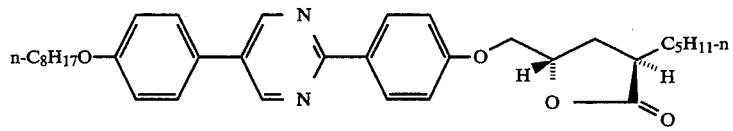

Phase transfer temperature:

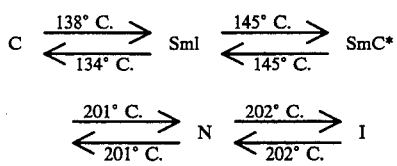

NMR (CDCl₃) δ: 0.4–3.0 (29H, m), 3.7–4.3 (4H, m), 4.82 (1H, m), 7.00 (4H, d, J=9.0 Hz), 7.50 (2H, d, J=9.0 Hz), 8.39 (2H, d, J=9.0 Hz), 8.85 (2H, s)

IR (nujol): 1778 cm⁻¹.

Preparation 9

The S isomer of glycidyl ether prepared in Preparation 4 (1.0 g), dimethyl n-heptylmalonate (1.267 g) and potassium t-butoxide (63 mg) are dissolved in dimethylformamide (10 ml) and t-butyl alcohol (10 ml), and the mixture is heated with stirring at 90° C. for 2 hours. After the reaction, the reaction mixture is treated in the same manner as described in Preparation 7 to give γ-lactone derivatives (705 mg). The product is a mixture of diastereomers and is purified by silica gel chromatography to give (2S, 4S) isomer and (2R, 4S) isomer.

(2S, 4S) isomer:

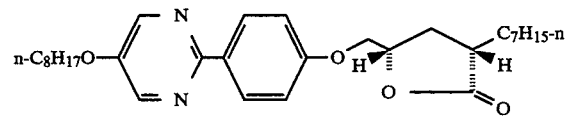

Phase transfer temperature:

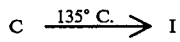

NMR (CDCl₃) δ: 0.4–3.1 (33H, m), 3.9–4.3 (4H, m), 4.66 (1H, m), 6.92 (2H, d, J=9.0 Hz), 8.25 (2H, d, J=9.0 Hz), 8.35 (2H, s)

IR (nujol): 1776 cm⁻¹.

(2R, 4S) isomer:

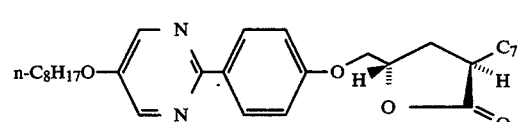

Phase transfer temperature:

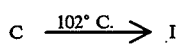

NMR (CDCl₃) δ: 0.4–3.1 (33H, m), 3.9–4.3 (4H, m), 4.77 (1H, m), 6.92 (2H, d, J=9.0 Hz), 8.25 (2H, d, J=9.0 Hz), 8.35 (2H, s)

IR (nujol): 1776 cm⁻¹.

PREPARATION OF THE COMPOUNDS (A)

Example 1

To a solution of lithium diisopropylamide, which is prepared from diisopropylamine (95 mg), n-butyl lithium (1.5 mol in n-hexane; 0.52 ml) and tetrahydrofuran (2 ml) by a conventional procedure, is added hexamethylphosphoric triamide (138 mg) at −78° C., followed by dropwise addition of a THF solution (5 ml) of a mixture (269 mg) of (2S, 4S) isomer and (2R, 4S) isomer of γ-lactone derivative prepared in Preparation 8. After the mixture is stirred at the same temperature for 40 minutes, methyl iodide (185 mg) is dropwise added to the mixture and the mixture is stirred for additional 2 hours. To the reaction solution is added a saturated aqueous solution of ammonium chloride and the mixture is warmed to room temperature. After extraction with ether (x2), the extract is dried with magnesium sulfate and distilled to remove the solvent. The residue is purified by silica gel chromatography to give γ-lactone derivatives, (2S, 4S) isomer (253 mg) and (2R, 4S) isomer (37 mg) of the following formulae:

(2S, 4S) isomer:

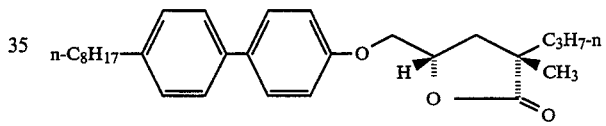

Phase transfer temperature:

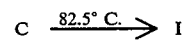

$[α]_D^{27}$ = +28.15° (c=1.058, CH₂Cl₂)

NMR (CDCl₃) δ: 0.85–0.98 (6H, m), 1.18–1.73 (19H, m), 2.00– 2.21 (2H, m), 2.62 (2H, t, J=7.70Hz), 4.04–4.17 (2H, m), 4.71–4.80 (1H, m), 6.93 (2H, d, J=8.79Hz), 7.21 (2H, d, J=7.33Hz ), 7.44 (2H, d, J=8.06Hz), 7.49 (2H, d, J=8.79 Hz)

(2R, 4S) isomer:

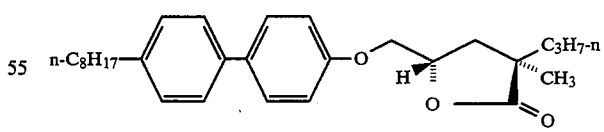

Phase transfer temperature:

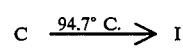

$[α]_D^{27}$ = +20.76° (c=1.247, CH₂Cl₂)

NMR (CDCl₃) δ: 0.86–0.98 (6H, m), 1.27–1.64 (19H, m), 2.03 (1H, dd, J=8.8Hz, J=12.8Hz), 2.35 (1H, dd, J=7.5Hz, J=12.8Hz), 2.62 (2H, t, J=7.3Hz), 4.06–4.18 (2H, m), 4.71–4.80 (1H, m), 6.95 (2H, d, J=8.79Hz), 7.22 (2H, d, J=8.43Hz), 7.45 (2H, d, J=8.06Hz), 7.50 (2H, d, J=8.79Hz).

Example 2

In the same manner as described in Example 1 except that diisopropylamine (70 mg), n-butyl lithium (1.5 mol/l in n-hexane; 0.30 ml), tetrahydrofuran (1 ml), hexamethylphosphoric triamide (100 mg), methyl iodide (130 mg) and a THF solution (2 ml) of a mixture (163 mg) of γ-lactone derivatives, (2R, 4R) isomer and (2S, 4R) isomer prepared in Preparation 6 are employed, there are prepared γ-lactone derivatives, (2R, 4R) isomer (130 mg) and (2S, 4R) isomer (22 mg) of the following formulae:

(2R, 4R) isomer:

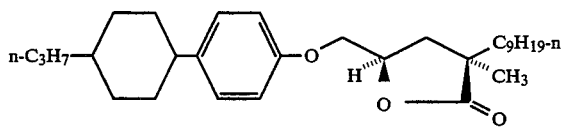

Phase transfer temperature:

$[\alpha]_D^{25} = -25.95°$ (c=1.013, CH$_2$Cl$_2$)
NMR (CDCl$_3$) δ: 0.87–1.66 (34H, m), 1.85 (2H, s), 1.88 (2H, s), 2.05 (1H, dd, J=6.96Hz, J=12.45Hz), 2.17 (1H, dd, J=9.89Hz, J=12.82Hz), 2.42 (1H, t, J=12.09Hz), 4.04–4.15 (2H, m), 4.71–4.81 (1H, m), 6.83 (2H, d, J=8.43Hz), 7.13 (2H, d, J=8.8Hz).

(2S, 4R) isomer:

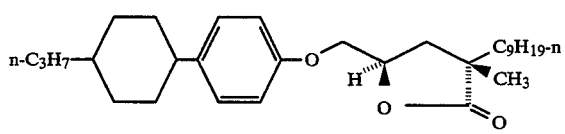

Phase transfer temperature:

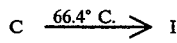

$[\alpha]_D^{25} = -17.15°$ (c=0.893 CH$_2$Cl$_2$)
NMR (CDCl$_3$) δ: 0.86–1.59 (34H, m), 1.83 (2H, s), 1.87 (2H, s), 2.01 (1H, dd, J=8.79Hz, J=13.79Hz), 2.34 (1H, dd, J=7.33Hz, J=12.82Hz), 2.41 (1H, t, J=12.09Hz), 4.02–4.12 (2H, m), 4.69–4.78 (1H, m), 6.82 (2H, d, J=8.80Hz), 7.12 (2H, d, J=8.79Hz).

Example 3

In the same manner as described in Example 1 except that diisopropylamine (80 mg), n-butyl lithium (1.5 mol/l in n-hexane; 0.41 ml), tetrahydrofuran (2 ml), hexamethylphosphoric triamide (130 mg), methyl iodide (170 mg) and a THF solution (5 ml) of a mixture (257 mg) of γ-lactone derivatives, (2S, 4S) isomer and (2R, 4S) isomer prepared in Preparation 9 are employed, there are prepared γ-lactone derivatives, (2S, 4S) isomer (90 mg) and (2R, 4S) isomer (20 mg) of the following formulae:

(2S, 4S) isomer:

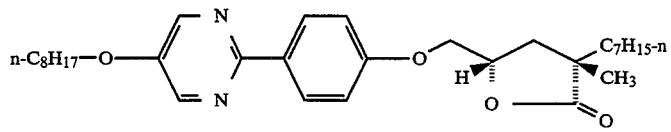

Phase transfer temperature:

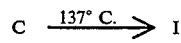

$[\alpha]_D^{25} = +29.53°$ (c=0.993, CH$_2$Cl$_2$)
NMR (CDCl$_3$) δ: 0.86–0.91 (6H, m), 1.29–1.67 (25H, m), 1.77–1.86 (2H, m), 2.07 (1H, dd, J=6.96Hz, J=12.83Hz), 2.20 (1H, dd, J=9.89Hz, J=13.19Hz), 4.07 (2H, t, J=6.59Hz), 4.11–4.23 (2H, m), 4.74–4.84 (1H, m), 6.97 (2H, d, J=9.16Hz), 8.29 (2H, d, J=9.16Hz), 8.41 (2H, s).

(2R, 4S) isomer:

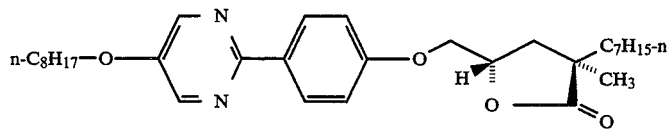

Phase transfer temperature:

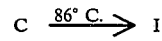

$[\alpha]_D^{25} = +25.99°$ (c=0.547, CH$_2$Cl$_2$)
NMR (CDCl$_3$) δ: 0.86–0.91 (6H, m), 1.15–1.62 (25H, m), 1.78–1.88 (2H, m), 2.05 (1H, dd, J=8.79Hz, J=13.19Hz), 2.36 (1H, dd, J=7.33Hz, J=13.19Hz), 2.36 (1H, dd, J=7.33Hz, J=13.19Hz), 4.08 (2H, t, J=6.60Hz), 4.10–4.22 (2H, m), 4.68–4.82 (1H, m), 6.98 (2H, d, J=8.79Hz), 8.29 (2H, d, J=9.16Hz), 8.42 (2H, s).

Example 4

In the same manner as described in Example 1 except that diisopropylamine (70 mg), n-butyl lithium (1.5 mol/l in n-hexane; 0.13 ml), tetrahydrofuran (2 ml), hexamethylphosphoric triamide (54 mg), methyl iodide (250 mg) and a THF solution (5 ml) of a mixture (80 mg) of γ-lactone derivatives, (2S, 4S) isomer and (2R, 4S) isomer prepared in Preparation 8 are employed, there are prepared γ-lactone derivatives, (2S, 4S) isomer (26 mg) and (2R, 4S) isomer (11 mg) of the following formulae:

(2S, 4S) isomer:

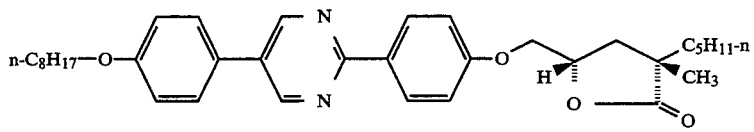

Phase transfer temperature:

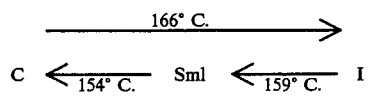

$[\alpha]_D^{29} = +15.12°$ (c=0.823, CH$_2$Cl$_2$)
NMR (CDCl$_3$) δ: 0.87–0.93 (6H, m), 1.26–1.68 (21H, m), 1.77–1.87 (2H, m), 2.09 (1H, dd, J=6.96Hz, J=12.82Hz), 2.22 (1H, dd, J=9.89Hz, J=12.82Hz), 4.01 (2H, t, J=6.60Hz), 4.15–4.26 (2H, m), 4.78–4.85 (1H, m), 7.01 (2H, d, J=8.79Hz), 7.03 (2H, d, J=8.79Hz), 7.54 (2H, d, J=8.79Hz), 8.43 (2H, d, J=9.16Hz), 8.93 (2H, s).

(2R, 4S) isomer:

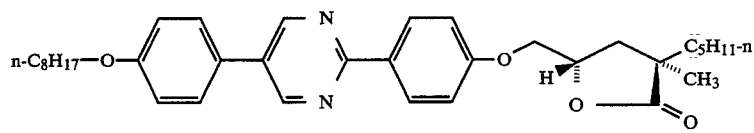

Phase transfer temperature:

$[\alpha]_D^{27} = +7.97°$ (c=0.483, CH$_2$Cl$_2$)
NMR (CDCl$_3$) δ: 0.88–0.92 (6H, m), 1.26–1.70 (21H, m), 1.76–1.87 (2H, m), 2.06 (1H, dd, J=8.79Hz, J=13.18Hz), 2.37 (1H, dd, J=7.32Hz, J=12.82Hz), 4.02 (2H, t, J=6.60Hz), 4.13–4.24 (2H, m), 4.75–4.83 (1H, m), 7.01 (2H, d, J=9.16Hz), 7.04 (2H, d, J=8.79Hz), 7.54 (2H, d, J=8.79Hz), 8.42 (2H, d, J=9.16Hz), 8.93 (2H, s).

LIQUID CRYSTAL COMPOSITION AND ELEMENT FOR OPTO-ELECTRONICS DEVICES

Example 5

The (2S, 4S) isomer of the γ-lactone derivative prepared in Example 1 of the following formula:

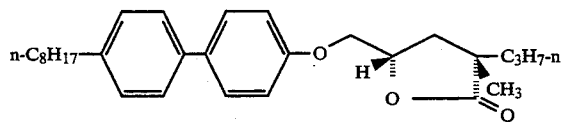

and a compound of the following formula:

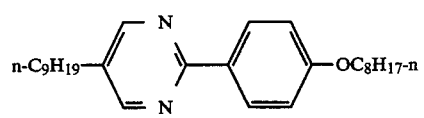

(1)

are mixed together at a weight ratio of 1:21.1 to give a liquid crystal composition.

The obtained liquid crystal composition is measured for phase transfer temperature by DSC measurement and observation with a polarization microscope, and as a result, the composition is found to show the following phase transfer temeperature:

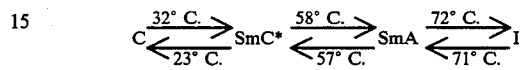

The liquid crystal composition is also measured for response speed using a cell (thickness of spacer: 2 μm) consisting of two glass substrates which are affixed with an ITO membrane, applied with polyimide and subjected to rubbing treatment, wherein the response speed is measured by sealing the composition in the cell and measuring a change in transmitted light when the cell is charged with a voltage of V$_{p-p}$=20 V. As a result, it is found that the response speed is 27 μsec (30° C.).

Example 6

The (2R, 4S) isomer of the γ-lactone derivative prepared in Example 1 of the following formula:

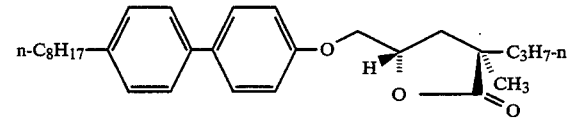

and the compound of the formula (1) prepared in Example 5 are mixed together at a weight ratio of 1:21.2 to give a liquid crystal composition. The obtained liquid crystal composition is measured for phase transfer temperature and response speed in the same manner as in Example 5 to give the following measurements:

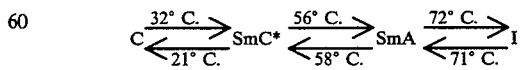

110 μsec (30° C.)

Example 7

The (2R, 4R) isomer of the γ-lactone derivative prepared in Example 2 of the following formula:

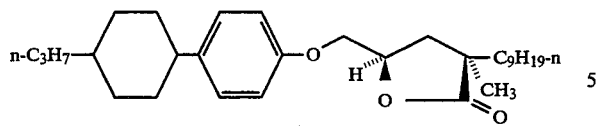

and the compound of the formula (1) prepared in Example 5 are mixed together at a weight ratio of 1:20.4 to give a liquid crystal composition. The obtained liquid crystal composition is measured for phase transfer temperature and response speed in the same manner as in Example 5 to give the following measurements:

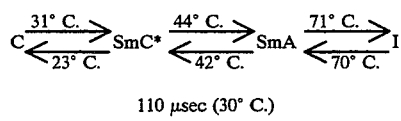

110 μsec (30° C.)

Example 8

The (2S, 4S) isomer of the γ-lactone derivative prepared in Example 3 of the following formula:

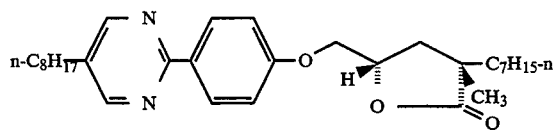

and the compound of the formula (1) prepared in Example 5 are mixed together at a weight ratio of 1:20.4 to give a liquid crystal composition. The obtained liquid crystal composition is measured for phase transfer temperature and response speed in the same manner as in Example 5 to give the following measurements:

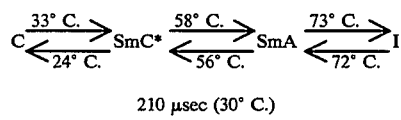

210 μsec (30° C.)

Example 9

The (2R, 4S) isomer of the γ-lactone derivative prepared in Example 4 of the following formula:

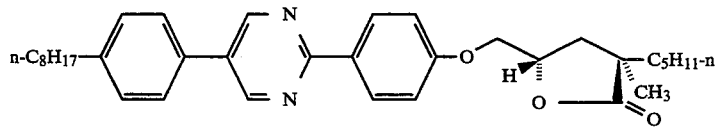

and the compound of the formula (1) prepared in Example 5 are mixed together at a weight ratio of 1:20.0 to give a liquid crystal composition. The obtained liquid crystal composition is measured for phase transfer temperature and response speed in the same manner as in Example 5 to give the following measurements:

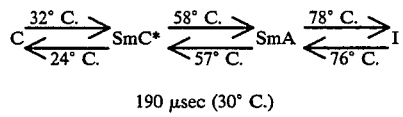

190 μsec (30° C.)

What is claimed is:

1. A liquid crystalline compound having an optically active γ-lactone ring of the general formula (A):

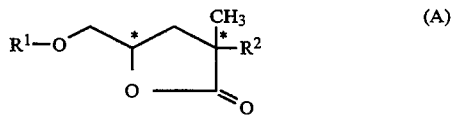

wherein $R^1$ is a group selected from the group consisting of

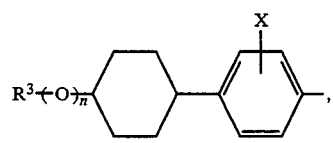

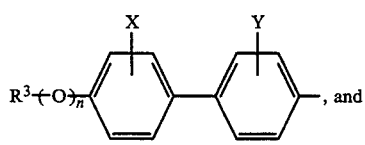

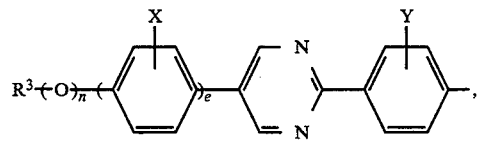

n and e are each independently 0 or 1, $R^3$ is an alkyl group having 1 to 15 carbon atoms or an alkenyl group having 2 to 15 carbon atoms, said alkyl and alkenyl groups having each optionally one or more asymmetric carbon atoms, X and Y are each hydrogen atom, a halogen atom and a cyano group, $R^2$ is an alkyl group having 1 to 15 carbon atoms or an alkenyl group having 2 to 15 carbon atoms, said alkyl and alkenyl groups having each optionally one or more asymmetric carbon atoms, and * means an asymmetric carbon atom provided that when $R^2$ is methyl, the carbon atom at 2-position is not an asymmetric carbon atom.

2. The compound according to claim 1, which is in the form of a racemic mixture.

3. The compound according to claim 1, wherein $R^2$ is an alkyl group having 3 to 8 carbon atoms, $R^3$ is an alkyl group having 3 to 9 carbon atoms, n is 0 or 1, and X and Y are each hydrogen atom.

* * * * *